(12) United States Patent
Arikawa et al.

(10) Patent No.: US 11,185,219 B2
(45) Date of Patent: Nov. 30, 2021

(54) OPHTHALMIC APPARATUS AND OPHTHALMIC APPARATUS CONTROL PROGRAM

(71) Applicant: NIDEK CO., LTD., Aichi (JP)

(72) Inventors: Toru Arikawa, Aichi (JP); Yoshihiro Ozaki, Aichi (JP); Hiroyuki Umano, Aichi (JP)

(73) Assignee: NIDEK CO., LTD., Aichi (JP)

( * ) Notice: Subject to any disclaimer, the term of this patent is extended or adjusted under 35 U.S.C. 154(b) by 220 days.

(21) Appl. No.: 16/096,556

(22) PCT Filed: Apr. 28, 2017

(86) PCT No.: PCT/JP2017/017102
§ 371 (c)(1),
(2) Date: Oct. 25, 2018

(87) PCT Pub. No.: WO2017/188456
PCT Pub. Date: Nov. 2, 2017

(65) Prior Publication Data
US 2019/0133436 A1     May 9, 2019

(30) Foreign Application Priority Data

Apr. 28, 2016 (JP) .............................. JP2016-091598
Apr. 28, 2016 (JP) .............................. JP2016-091599
Apr. 28, 2016 (JP) .............................. JP2016-091600

(51) Int. Cl.
*A61B 3/00* (2006.01)
*A61B 3/117* (2006.01)
(Continued)

(52) U.S. Cl.
CPC .......... *A61B 3/0008* (2013.01); *A61B 3/0075* (2013.01); *A61B 3/0083* (2013.01);
(Continued)

(58) Field of Classification Search
CPC ....... A61B 3/0083; A61B 3/117; A61B 3/152; A61B 3/0008; A61B 3/0075; A61B 3/14;
(Continued)

(56) References Cited

U.S. PATENT DOCUMENTS

| 5,909,269 A | 6/1999 | Isogai |
|---|---|---|
| 2009/0195750 A1 | 8/2009 | Isogai |

(Continued)

FOREIGN PATENT DOCUMENTS

| JP | H10216089 A | 8/1998 |
|---|---|---|
| JP | 2005287752 A | 10/2005 |

(Continued)

OTHER PUBLICATIONS

International Search Report dated Jun. 20, 2017 filed in PCT/JP2017/017102.

*Primary Examiner* — Brandi N Thomas
(74) *Attorney, Agent, or Firm* — Rankin, Hill & Clark LLP

(57) ABSTRACT

A technical object is to provide an ophthalmic apparatus and an ophthalmic apparatus control program that are capable of appropriately performing alignment in a wide range. An ophthalmic apparatus that examines an examinee's eye includes: an optometry unit that examines the examinee's eye; drive means that adjusts a relative position between the optometry unit and the examinee's eye; an illuminating optical system including a first illuminating optical system for illuminating an anterior segment of the examinee's eye and a second illuminating optical system for illuminating a wider range than the first illuminating optical system; an imaging optical system including a first imaging optical system for imaging the anterior segment of the examinee's eye and a second imaging optical system for imaging a wider range than the first imaging optical system; and control means that controls an illuminating state with respect to the (Continued)

anterior segment between anterior segment illumination by the first illuminating optical system and wide range illumination by the second illuminating optical system.

8 Claims, 9 Drawing Sheets

(51) Int. Cl.
    *A61B 3/14*     (2006.01)
    *A61B 3/15*     (2006.01)

(52) U.S. Cl.
    CPC .............. *A61B 3/117* (2013.01); *A61B 3/14* (2013.01); *A61B 3/152* (2013.01)

(58) Field of Classification Search
    CPC ..... A61B 3/0025; A61B 3/0091; A61B 3/102; A61B 3/1025; A61B 3/11; A61B 3/112; A61B 3/113; A61B 3/1225; A61B 3/15; A61B 3/135
    See application file for complete search history.

(56) References Cited

U.S. PATENT DOCUMENTS

2014/0320810 A1    10/2014   Fukuma
2015/0313468 A1*  11/2015   Okada ..................... A61B 3/15
                                          351/208

FOREIGN PATENT DOCUMENTS

JP         2009201981 A2    9/2009
JP         2013066760 A     4/2013
JP         2014200680 A    10/2014

* cited by examiner

OPHTHALMIC APPARATUS AND OPHTHALMIC APPARATUS CONTROL PROGRAM

TECHNICAL FIELD

The present disclosure relates to an ophthalmic apparatus for examining an examinee's eye and an ophthalmic apparatus control program.

BACKGROUND ART

For example, an eye refractive power measurement apparatus, a corneal curvature measurement apparatus, an eye pressure measurement apparatus, a fundus camera, an OCT, and an SLO are known as conventional ophthalmic apparatuses. In these ophthalmic apparatuses, typically, an optometry unit is aligned at a predetermined position with respect to an examinee's eye by moving the optometry unit in up-down, right-left, and front-back directions with respect to the examinee's eye by operating an operating member such as a joystick (refer to Patent Literature 1).

Further, in conventional ophthalmic apparatuses, there is proposed an ophthalmic apparatus that photographs the face of an examinee to perform alignment in a wide range (refer to Patent Literature 2).

CITATION LIST

Patent Literature

Patent Literature 1: JP 2013-066760 A
Patent Literature 2: JP 10-216089 A

SUMMARY OF THE INVENTION

As a first problem, an ophthalmic apparatus currently on the market requires an operation of an operating member by an examiner until an examinee's eye is found. Further, an apparatus capable of performing alignment in a wide range has not been achieved. That is, there may be various items to be considered in achieving the apparatus capable of performing alignment in a wide range. In view of these items, the inventors of the present invention have devised a prototype of the apparatus capable of performing alignment in a wide range.

As a second problem, in conventional apparatuses, alignment to a predetermined position with respect to an examinee's eye cannot be performed only with a target of the examinee's eye in some cases.

As a third problem, in conventional apparatuses, the face of an examinee cannot be excellently photographed depending on the position of an optometry unit in some cases.

In view of the above problems, it is a technical object of the present disclosure to provide an ophthalmic apparatus and an ophthalmic apparatus control program that solve at least one of the problems in the conventional technique.

In order to solve the above first problem, a first embodiment according to the present disclosure has the configuration as described below.

In order to solve the above second problem, a second embodiment according to the present disclosure has the configuration as described below.

In order to solve the above third problem, a third embodiment according to the present disclosure has the configuration as described below.

DESCRIPTION OF THE EMBODIMENTS

First Embodiment

Figure 1:
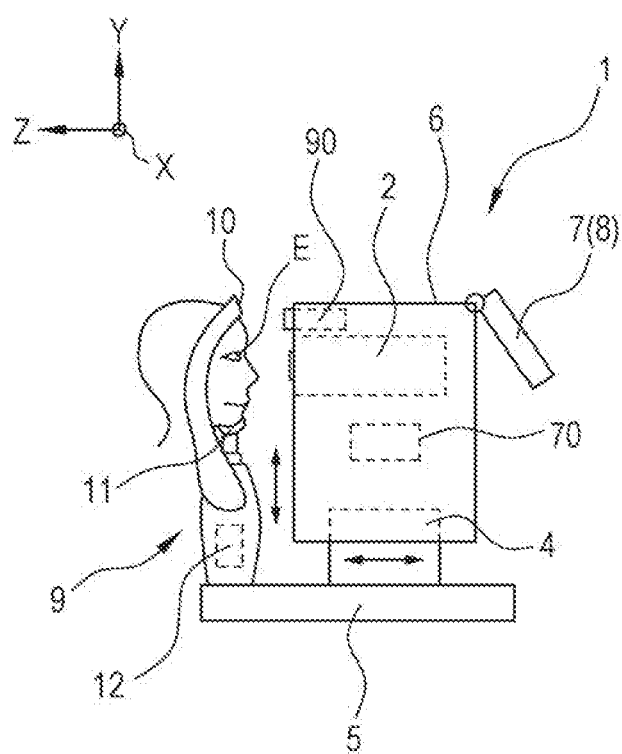
FIG. 1 is a schematic diagram illustrating the appearance of the present exemplary embodiment.

Hereinbelow, an ophthalmic apparatus according to a first embodiment will be described. The ophthalmic apparatus according to the first embodiment may include an optometry unit (e.g., an optometry unit 2), a drive unit (e.g., a drive unit 4), and a control unit (e.g., a control unit 70).

The optometry unit may be provided for examining an examinee's eye. The optometry unit may include, for example, an optometry optical system as a configuration for examining an examinee's eye. For example, the optometry unit may be either a configuration for measuring an examinee's eye or a configuration for photographing an examinee's eye. The configuration for examining an examinee's eye is not limited to the optometry optical system, and another measuring system (e.g., an ultrasonic tonometer) or another photographing system (e.g., an ophthalmic ultrasonic photographing apparatus) may be provided.

The drive unit may be provided for adjusting a relative position between the optometry unit and an examinee's eye. For example, the drive unit may be either a drive unit that moves the optometry unit with respect to an examinee's eye or a drive unit that moves an examinee's eye with respect to the optometry unit (e.g., a chin rest moving mechanism).

The control unit may, for example, be a processor. The control unit may control each configuration included in the ophthalmic apparatus or may perform various calculation processes. The control unit may be operated by a control program for controlling the ophthalmic apparatus according to the present embodiment.

Further, the ophthalmic apparatus according to the first embodiment may include an illuminating optical system (e.g., a target projecting optical system 50) for illuminating at least an anterior segment and an imaging optical system (e.g., an anterior segment photographing optical system 60) for imaging at least the anterior segment. The imaging optical system may be an imaging optical system for capturing a frontal image including the anterior segment. For example, the imaging optical system may be an imaging optical system for capturing the frontal image including the anterior segment by a two-dimensional imaging device. The illuminating optical system may be provided for illuminating an area including the anterior segment, the area being imaged by the imaging optical system. Hereinbelow, an example of the embodiment according to the illuminating optical system and the imaging optical system will be described.

<Illuminating Optical System>

The illuminating optical system may include a first illuminating optical system for illuminating the anterior segment of the examinee's eye and a second illuminating optical system for illuminating the anterior segment of the examinee's eye in a wider range than the first illuminating optical system. The second illuminating optical system may be disposed at a different position with respect to at least a part of the first illuminating optical system. In this case, at least a part of the second illuminating optical system may be disposed at a position farther from an examination axis of the optometry unit than the first illuminating optical system is. Further, the second illuminating optical system may also serve as the first illuminating optical system.

At least either the first illuminating optical system or the second illuminating optical system may be an illuminating optical system that performs illumination with infrared light. In this case, for example, an infrared light source may be used, or a filter that transmits infrared light and cuts visible light may be used together with a visible light source. At least either the first illuminating optical system or the second illuminating optical system may also serve as a target projecting optical system for projecting an alignment target to the examinee's eye.

The first illuminating optical system may be an anterior segment illuminating optical system. An illumination range of the first illuminating optical system may, for example, be an illumination range including at least the pupil, the sclera, and the eyelashes of the examinee's eye.

The second illuminating optical system has a wider illumination range than the first illuminating optical system. The second illuminating optical system may illuminate an area including the anterior segment in a wider range than the first illuminating optical system. The second illuminating optical system may, for example, be a face illuminating optical system. The illumination range of the second illuminating optical system may be an illumination range capable of illuminating the face of an examinee including at least both eyes. Further, the illumination range of the second illuminating optical system may be an illumination range capable of illuminating one eye in a wider range than the first illuminating optical system.

The illuminating optical system may separately include the first illuminating optical system and the second illuminating optical system. Accordingly, excellent illumination is performed in alignment by a first imaging optical system and alignment by a second imaging optical system, and the alignment can be smoothly performed.

As an example of a configuration for having a wide illumination range, the second illuminating optical system is disposed at a position farther from the examination axis of the optometry unit than the first illuminating optical system is so that the second illuminating optical system can illuminate the examinee in a wide range. In this case, the distance in the up-down and right-left directions between an optical axis of the second imaging optical system and the second illuminating optical system may be longer than the distance in the up-down and right-left directions between an optical axis of the first imaging optical system and the first illuminating optical system.

As an example of the configuration for having a wide illumination range, the second illuminating optical system may be a diffusion optical system and may include a light diffusing optical member (e.g., a light diffusing plate) for diffusing light emitted from an illuminating light source to a wide range. Accordingly, it is possible to illuminate the face of the examinee in a wide range. The light diffusing optical member may, for example, be a lens that diffuses light. Of course, an illuminating light source having a light diffusing property may be used.

The second illuminating optical system may include a plurality of illuminating light sources. The illuminating light sources are disposed right and left with respect to the second imaging optical system so that an illumination balance in the right-left direction is ensured. The right and left illuminating light sources may be disposed at positions separated from each other by more than a predetermined interpupillary distance (e.g., an average interpupillary distance of human eyes). Accordingly, it is possible to illuminate both eyes in a wide range.

In this case, for example, the illuminating light sources may be symmetrically disposed right and left with respect to the first imaging optical system or symmetrically disposed right and left with respect to the second imaging optical system. Further, a plurality of illuminating light sources may be arrayed up and down, which ensures an illumination balance in the up-down direction. A surface emitting illuminating light source whose longitudinal direction corresponds to the up-down direction may be used. Further, the illuminating light source may be a ring-like light source. Of course, the disposition configuration of the illuminating light source can be variously modified and not limited to the above configurations.

Further, in the disposition of the illuminating light source, the optical axis of the illuminating light source may be titled toward the examinee's eye with respect to the examination axis of the optometry unit. Accordingly, it is possible to excellently illuminate both examinee's eyes. Further, the second illuminating optical system may be disposed at a position projecting toward the examinee's eye with respect to an optometry window. Accordingly, the illuminating optical system is disposed at the position close to the examinee's eye, and a sufficient illuminating light amount is ensured.

<Imaging Optical System>

The imaging optical system may include the first imaging optical system for imaging the anterior segment of the examinee's eye and the second imaging optical system for imaging the anterior segment of the examinee's eye in a wider range than the first imaging optical system. The second imaging optical system may be disposed at a different position with respect to the first imaging optical system. The first imaging optical system and the second imaging optical system may be disposed inside a housing of the optometry unit. Alternatively, the first imaging optical system may be disposed inside the housing of the optometry unit, and the second imaging optical system may be disposed outside the housing of the optometry unit. When the imaging optical system is disposed inside the housing, the imaging optical system images the examinee's eye through the optometry window included in the optometry unit. When the imaging optical system is disposed outside the housing, the imaging optical system images the examinee's eye without through the optometry window. Of course, the first imaging optical system and the second imaging optical system may be both disposed outside an examinee-side housing face. Further, the second imaging optical system may also serve as the first imaging optical system.

The first imaging optical system may be used for imaging the anterior segment of the examinee's eye illuminated by the first illuminating optical system. The second imaging optical system may be used for imaging the anterior segment of the examinee's eye illuminated by the second illuminating optical system.

The first imaging optical system may be an anterior segment imaging optical system. An imaging range of the first imaging optical system may, for example, be an imaging range including at least the pupil, the sclera, and the eyelashes of the examinee's eye. The anterior segment imaging optical system may be used for imaging the anterior segment illuminated by the anterior segment illuminating optical system.

The second imaging optical system has a wider imaging range than the first imaging optical system. The second imaging optical system may, for example, be a face imaging optical system. The imaging range of the second imaging optical system may be an imaging range capable of imaging the face of the examinee including at least both eyes. The second imaging optical system may be used for imaging the face of the examinee illuminated by the second illuminating optical system. For example, the face imaging optical system may be used for imaging the face illuminated by the face illuminating optical system.

Further, the imaging range of the second imaging optical system may be an imaging range capable of imaging one eye in a wider range than the first imaging optical system. The second imaging optical system may be used for imaging one eye of the examinee illuminated by the second illuminating optical system in a wider range than the first imaging optical system.

The imaging optical system may separately include the first imaging optical system and the second imaging optical system. Accordingly, severe alignment using the first imaging optical system and rough alignment using the second imaging optical system can be performed in a suitable manner.

As an example of a configuration for having a wide imaging range, the second imaging optical system may include a fisheye lens. A smaller size and a wider angle can be both achieved by the fisheye lens.

<Use for Alignment>

The control unit may display an anterior segment image based on an imaging signal from the first imaging optical system on a display unit or may use the anterior segment image for automatic alignment of the optometry unit with respect to the examinee's eye. Further, the control unit may display an image based on an imaging signal from the second imaging optical system on the display unit or may use the image for automatic alignment of the optometry unit with respect to the examinee's eye. In this case, the control unit may perform the automatic alignment with respect to the examinee's eye by controlling the drive unit on the basis of the imaging signals from the first imaging optical system and the second imaging optical system.

Further, the control unit may automatically start an optometry operation after the completion of the automatic alignment. In this case, for example, the control unit may automatically emit a trigger signal for starting an optometry operation using the optometry unit and actuate the optometry unit (e.g., the optometry optical system) in response to the trigger signal.

When the relative position between the examinee's eye and the optometry unit is automatically adjusted on the basis of an imaging signal from the imaging optical system, automatic alignment may be performed by moving at least either the optometry unit or a chin rest on the basis of the imaging signal. In this case, at least either the drive unit for moving the optometry unit or the drive unit for moving the chin rest may be controlled to drive by the control unit.

When the distance between the examinee's eye and the optometry unit is long, the control unit may operate automatic alignment based on an imaging signal from the second imaging optical system. Further, when the distance between the examinee's eye and the optometry unit is short, the control unit may operate automatic alignment based on an imaging signal from the first imaging optical system.

<Illumination Control>

The control unit may control an illuminating state with respect to the anterior segment between anterior segment illumination by the first illuminating optical system and anterior segment illumination in a wide range by the second illuminating optical system. Accordingly, an illuminating state suitable for at least either the alignment by the first imaging optical system or the alignment by the second imaging optical system is set, and excellent alignment can be performed.

For example, the control unit may change the illuminating state with respect to the anterior segment between the anterior segment illumination by the first illuminating optical system and the anterior segment illumination in a wide range by the second illuminating optical system. The anterior segment illumination may be used in the alignment using the first imaging optical system, and the wide range illumination may be used in the alignment using the second imaging optical system.

It is only required that illumination different from the wide range illumination by the second illuminating optical system be performed at any timing in the anterior segment illumination by the first illuminating optical system, and the change does not necessarily have to be performed at the time of switching between the alignment by the first imaging optical system and the alignment by the second imaging optical system. In this case, the control unit may perform switching between the anterior segment illumination by the first illuminating optical system and the face illumination by the second illuminating optical system. Accordingly, for example, it is possible to perform illumination switching according to the alignment control and smoothly perform the alignment.

As an example of the control of the illuminating state described above, the control unit may restrict the illumination by the second illuminating optical system in the alignment of the optometry unit using the first imaging optical system. Accordingly, it is possible to reduce the influence by the second illuminating optical system. For example, in an alignment mode using the first imaging optical system (hereinbelow, referred to as the first alignment), the control unit may operate the first illuminating optical system to perform the anterior segment illumination and restrict the wide range illumination by the second illuminating optical system. Accordingly, noise (e.g., a raster in the anterior segment and an increase in the light amount in the entire image) caused by the second illuminating optical system is restricted in the anterior segment image, and appropriate anterior segment alignment can be performed.

As an example of the control of the illuminating state described above, the illumination by the first illuminating optical system may be restricted in the alignment of the optometry unit using the second imaging optical system. Accordingly, it is possible to reduce the influence by the first illuminating optical system. For example, in an alignment mode using the second imaging optical system (hereinbelow, referred to as the second alignment), the control unit may operate the second illuminating optical system to perform the wide range illumination and restrict the anterior segment illumination by the first illuminating optical system. Accordingly, noise (e.g., a raster in the anterior segment and an increase in the light amount in the entire image) caused by the first illuminating optical system is restricted in the wide range anterior segment image, and appropriate wide range alignment can be performed.

As a specific method for restricting the wide range illumination, for example, illuminating light to the examinee may be entirely blocked. In this case, the illuminating light source may be turned off, or the illuminating light may be blocked by driving a shutter. Further, the illuminating light to the examinee may not be entirely blocked, but reduced to a degree by which noise light is reduced. In this case, the light amount of the illuminating light source may be reduced, or part of the illuminating light may be reduced by a dimmer filter. Any of the above methods can be used as a method for restricting the anterior segment illumination.

The ophthalmic apparatus according to the present embodiment may be, in addition to the ophthalmic apparatus having both a function of restricting the wide range illumination in the first alignment and a function of restricting the anterior segment illumination in the second alignment, an ophthalmic apparatus having only the function of restricting the wide range illumination or an ophthalmic apparatus having only the function of restricting the anterior segment illumination.

When the second illuminating optical system is disposed at the different position with respect to at least a part of the first illuminating optical system, the control unit may control the illuminating state with respect to the examinee between the anterior segment illumination by the first illuminating optical system and the wide range illumination by the second illuminating optical system by performing switching between the operation of the first illuminating optical system and the operation of the second illuminating optical system.

<Illumination Switching Control>

The control unit may control the illuminating state with respect to the examinee between the anterior segment illumination by the first illuminating optical system and the wide range anterior segment illumination by the second illuminating optical system on the basis of the imaging signal from the imaging optical system. Accordingly, alignment can be smoothly performed.

In this case, for example, the control unit may restrict the wide range illumination by the second illuminating optical system on the basis of the imaging signal from the first imaging optical system. In this case, the control unit may determine whether to restrict the wide range illumination on the basis of the imaging signal from the first imaging optical system and restrict the wide range illumination in accordance with a result of the determination.

For example, the control unit may restrict the wide range illumination on the basis of an alignment detection result with respect to the eye based on the imaging signal from the first imaging optical system. As the alignment detection result, for example, the control unit may determine whether the examinee's eye has been detected by an analyzing process different from target detection on the basis of the imaging signal from the first imaging optical system and restrict the wide range illumination when it is determined that the examinee's eye has been detected. The analyzing process different from the target detection may, for example, be a process for detecting a feature portion (e.g., the pupil, the iris, the sclera, and the blood vessel) of the examinee's eye. Further, the control unit may determine whether an alignment target from the eye has been detected on the basis of the imaging signal from the first imaging optical system and restrict the second illuminating optical system when it is determined that the alignment target has been detected. The present embodiment is not limited to the above technique as long as it is determined that the eye has been detected by a corneal reflex by the illuminating optical system or the target projecting optical system or the feature portion of the eye on the basis of the imaging signal from the first imaging optical system.

The alignment detection result is not limited to the above, and the wide range illumination may be restricted when an alignment deviation which is detected using the first imaging optical system satisfies an allowable range. In this case, the allowable range may have a condition that is relaxed as compared to an allowable range of the generation of an optometry starting trigger. Accordingly, in precise alignment for optometry start, the wide range illumination is restricted, and the alignment with respect to the examinee's eye can be accurately performed.

As described above, the automatic alignment based on a result of the alignment detection using the first imaging optical system can be smoothly performed by restricting the wide range illumination on the basis of the alignment detection result. For example, when an alignment state of the optometry unit with respect to the examinee's eye is detected using the pupil or the alignment target, the wide range illumination is restricted in conjunction with detection of the pupil or the alignment target, so that alignment detection thereafter can be performed with a reduced influence of noise light. Thus, it is possible to smoothly perform automatic alignment.

The control unit may determine whether to restrict the wide range illumination or to restrict the anterior segment illumination on the basis of the imaging signal from the first imaging optical system and restrict the illumination in accordance with a result of the determination. For example, the control unit may restrict the wide range illumination when the examinee's eye has been detected in the imaging signal from the first imaging optical system and restrict the anterior segment illumination when the examinee's eye has not been detected. Accordingly, it is possible to smoothly perform illumination restriction corresponding to each alignment.

In the above description, the face illumination is restricted on the basis of the imaging signal from the first imaging optical system. However, the present embodiment is not limited thereto, and the wide range illumination may be restricted on the basis of the imaging signal from the second imaging optical system. For example, the distance between the optical axes of the first imaging optical system and the second imaging optical system is previously known. Thus, the control unit can detect the positional relationship between the first imaging optical system and the optometry unit by multiplying a deviation in the alignment between the examinee's eye and the optometry unit, the deviation being detected by the second imaging optical system, by an offset corresponding to the distance between the optical axes. Thus, when the alignment deviation reaches an allowable range in the positional relationship between the first imaging optical system and the optometry unit, the positional relationship being detected by the second imaging optical system, the control unit may determine that the eye has been detected by the first imaging optical system and restrict the wide range illumination.

When the control unit switches the imaging optical system used in the alignment control between the first imaging optical system and the second imaging optical system, the control unit may perform switching between the anterior segment illumination by the first illuminating optical system and the wide range illumination by the second illuminating optical system. Accordingly, it is possible to smoothly perform each alignment. Also when the imaging optical system used in the alignment control is set to one of the first imaging optical system and the second imaging optical system, the other imaging optical system may operate in a background.

In the above description, an example in which the illumination is restricted on the basis of the imaging signal from the imaging optical system has been described. However, the present embodiment is not limited thereto, and the control unit may restrict the illumination on the basis of an operation signal from the operating unit operated by the examiner.

<Modifications>

In the above first embodiment, when the illuminating state is switched between the first alignment and the second alignment, the illuminating state may be alternately switched between the anterior segment illumination by the first illuminating optical system and the wide range illumination by the second illuminating optical system. In this case, the control unit may detect the alignment state with respect to the examinee's eye on the basis of an imaging signal acquired by the second imaging optical system during the wide range illumination. Further, the control unit may detect the alignment state with respect to the examinee's eye on the basis of an imaging signal acquired by the first imaging optical system during the anterior segment illumination. In this case, a reaction speed of alignment is slightly reduced. However, the influence by the other illumination is reduced, and excellent alignment can be performed.

The control unit may perform continuous illumination by the second illuminating optical system in the second alignment and alternately perform the wide range illumination by the second illuminating optical system and the anterior segment illumination by the first illuminating optical system in the first alignment.

The present embodiment can also be applied to the case where a single illuminating optical system performs anterior segment illumination and face illumination. For example, the second illuminating optical system may also serve as the first illuminating optical system.

In this case, the control unit may change the illuminating state with respect to the anterior segment between the anterior segment illumination and the wide range illumination. For example, in the first alignment, the control unit may change an illuminating state by the second illuminating optical system with respect to an illuminating state in the case where the second alignment is performed. Accordingly, for example, also when the second illuminating optical system also serves as the first illuminating optical system, illumination suitable for the first alignment can be performed.

In the case of a structure in which a shortage of the amount of illuminating light occurs when the first alignment is performed, the control unit may increase the amount of illuminating light by the second illuminating optical system so as to be larger than the amount of light in the face alignment. On the other hand, in the case of a structure in which an excess of the amount of illuminating light occurs when the first alignment is performed, the control unit may reduce the amount of illuminating light by the second illuminating optical system so as to be smaller than the amount of light in the first alignment. When the illuminating state is changed, for example, an increase or decrease of light from the light source may be performed. When a plurality of light sources are used, a configuration of selecting a light source used for illumination may be used.

The present embodiment can also be applied to the case where a single imaging optical system performs anterior segment imaging and face imaging. For example, the second imaging optical system capable of capturing an image including both examinee's eyes may be disposed, and the control unit may perform rough automatic alignment and severe automatic alignment on the basis of an imaging signal from the second imaging optical system.

In this case, the control unit may switch the illuminating state by the first illuminating optical system and the second illuminating optical system. For example, the control unit may perform the wide range illumination using the second illuminating optical system in the rough automatic alignment (when the distance between the optometry unit and the eye is long). Further, the control unit may perform the anterior segment illumination using the first illuminating optical system in the severe automatic alignment (when the distance between the optometry unit and the eye is short).

Second Embodiment

Hereinbelow, an ophthalmic apparatus of a second embodiment will be described. The ophthalmic apparatus of the second embodiment mainly includes an optometry unit (e.g., an optometry unit 2), a drive unit (e.g., a drive unit 4), and a face photographing unit (e.g., a face photographing 90). The optometry unit, for example, incudes an optometry optical system and examines an examinee's eye. The drive unit moves the optometry unit relative to the examinee's eye. The face photographing unit photographs the face of an examinee. The face photographing unit may photographs, for example, both right and left eyes of the examinee. A photographing optical axis of the face photographing unit is disposed at a position displaced either right or left from an examination optical axis of an optometry optical system.

Accordingly, even when the optometry unit for examining the examinee's eye is moved either right or left, the face photographing unit can be disposed near the center of the face of the examinee. Accordingly, the face photographing unit easily photographs both eyes of the examinee. For example, when the optometry unit measures one eye and then moves to the other eye, eye information obtained from the face image can be used by photographing the face including both eyes of the examinee. Further, for example, even when the optometry unit is disposed near one eye, the optometry unit can be smoothly moved to the other eye by using the face image.

The face photographing unit may be disposed in such a manner that the face photographing means is located between the left eye and the right eye of the examinee when the optometry unit is moved to a predetermined position which is previously set. The predetermined position may be an initial position. The predetermined position is set at, for example, a position displaced either right or left from a machine center position in order to quickly measure either the right eye or the left eye. The machine center position may, for example, be a center position in the right-left direction of a driving range of the drive unit or may be a position of a right-left symmetry axis of an apparatus body (e.g., a base or a face support unit). For example, the face photographing unit may be disposed in such a manner that the machine center of the apparatus body (e.g., the base) corresponds to the position in the right-left direction when the optometry unit is moved to the predetermined position. Accordingly, the face photographing unit can photographs both eyes of the examinee when the optometry unit 2 is disposed at the predetermined position. The right-left direction is, for example, an eye width direction of the examinee.

The face photographing unit may be disposed at a position displaced either right or left from the examination optical axis by a single-eye interpupillary distance (the half of the interpupillary distance). The initial position may be set at, for example, a position displaced from the machine center of the apparatus by the single-eye interpupillary distance in order to reduce the alignment time. In such a case, the face photographing unit may be disposed at a position displaced in the right-left direction with respect to the examination optical axis so that the face photographing unit is disposed at the position of the machine center in the right-left direction when the examination optical axis is disposed at the position displaced right or left by the single-eye interpupillary distance with respect to the machine center. In this case, as the interpupillary distance, a predetermined interpupillary distance may be used, or, for example, an average interpupillary distance in human eyes (typically, 64 mm) may be used. However, of course, the interpupillary distance is not limited thereto.

The face photographing unit may be disposed in such a manner that the photographing optical axis is parallel to the examination optical axis. Accordingly, both examinee's eyes are easily photographed when the optometry unit is disposed at the initial position and the face photographing unit is located at the front of the face of the examinee.

The apparatus may include a control unit (e.g., a control unit 70). The control unit may, for example, detect position coordinates of the examinee's eye on the basis of a face image captured by the face photographing unit. At this time, the control unit may detect the position of the examinee's eye from the image remaining distorted due to the influence of a photographing lens (e.g., an imaging lens 92). Further, the control unit may correct the position coordinates in accordance with the distortion of the face image. It is possible to smoothly acquire the position coordinates of the examinee's eye from the face image as compared to the case where the distortion of the entire face image is corrected, by detecting the position coordinates of the examinee's eye from the distorted face image and then correcting the position coordinates in accordance with the distortion of the image in this manner.

For example, the control unit may move the optometry unit to the initial position by controlling the drive unit. Further, the control unit may photograph the face including both right and left eyes in a state where the optometry unit is located at the initial position by controlling the face photographing unit. Further, for example, the control unit may move the optometry unit relative to the examinee's eye by controlling the drive unit on the basis of the face image captured by the face photographing unit.

Further, for example, the control unit may detect both eyes from the face image and obtain the position coordinates of the eyes. When the position coordinates of both eyes are obtained, the control unit 70 may perform rough alignment on the basis of the position coordinates of the eyes when a measurement target eye is switched between the right and left eyes. In this manner, both the examinee's eyes can be photographed in a state where the optometry unit can be promptly aligned with respect to the eye to be measured first by moving the optometry unit either right or left. Accordingly, not only positional information of the eye which has been measured first, but also position information of the eye to be measured next can be acquired, and switching between the right and left eyes can be smoothly performed.

Third Embodiment

Hereinbelow, a third embodiment will be described. An ophthalmic apparatus of the third embodiment mainly includes, for example, an optometry unit (e.g., an optometry unit 2), an anterior segment photographing unit (e.g., an anterior segment photographing optical system 60), a target projecting unit (e.g., a target projecting optical system 50), a drive unit (e.g., a drive unit 4), and a control unit (e.g., a control unit 70). The optometry unit, for example, examines an examinee's eye. The anterior segment photographing unit, for example, photographs the anterior segment of the examinee's eye. The target projecting unit, for example, projects a target for detecting an alignment state between the examinee's eye and the optometry unit onto the examinee's eye. The drive unit moves the optometry unit relative to the examinee's eye. The control unit, for example, controls the drive unit.

The control unit, for example, performs a target detecting process in parallel with an image analyzing process different from the target detecting process with respect to an anterior segment image. In this case, the control unit 70 controls the drive unit on the basis of results of the target detecting process and the image analyzing process. Accordingly, it is possible to more reliably perform alignment between the examinee's eye and the optometry unit.

The target detecting process is, for example, a process for detecting a target which is projected onto the anterior segment of the examinee's eye by the target projecting unit. In a detection method by the image analyzing process different from the target detecting process, for example, a feature portion of the examinee's eye may be detected from the anterior segment image. The feature portion of the examinee's eye may, for example, be at least any of the pupil, the iris, and the sclera. In the detection method by the image analyzing process different from the target detecting process, for example, a focus evaluation value may be detected on the basis of at least a part of the anterior segment image by a method different from the target detection.

A detection range of the examinee's eye by the image analyzing process different from the target detecting process may be set to be wider than a detection range in which the target detection is performed. For example, detecting the feature portion such as the pupil has a higher possibility that the detection can be performed even when there is blurring or an eclipse by iris in an image and a higher detection range than the target detection.

When the target has been detected, the control unit may perform the alignment between the examinee's eye and the optometry unit on the basis of a result of the detection of the target. Further, when the target has not been detected, and the examinee's eye has been detected by the image analyzing process, the alignment between the examinee's eye and the optometry unit in the up-down and right-left directions may be performed on the basis of a result of the detection by the image analyzing process. The case where the target has been detected may be any of the case where the pupil has not been detected and the target has been detected, and the case where the target and the pupil have been detected.

A focus analyzing process may be performed as the image analyzing process. The focus analyzing process may, for example, be a process for obtaining an evaluation value for evaluating a focus state by analyzing the anterior segment image. In this case, the control unit may control the drive unit on the basis of a detection result of the target or an analysis result of the focus analyzing process.

The evaluation value may, for example, be an evaluation value that varies in accordance with the distance with respect to a focused position. In this case, an evaluation value that becomes higher as approaching the focused position may be used as the evaluation value. Further, an evaluation value that becomes lower as approaching the focused position may be used as the evaluation value. In this case, in the image analyzing process, an image feature (e.g., the definition of the image) having a characteristic of varying in accordance with the distance with respect to the focused position may be acquired. The drive unit may be controlled in accordance with the acquired image feature.

The control unit may perform Z-alignment which performs the target detecting process in parallel with the focus analyzing process while moving the optometry unit forward or backward in the Z direction. Further, when the target has not been detected and the focus evaluation value has largely varied with respect to an evaluation value corresponding to the focused position by more than a predetermined amount, the control unit 70 may reverse the moving direction and repeat the Z-alignment again. Accordingly, when the optometry unit has passed a position where the target should be detected, the target detection can be tried again.

The control unit may perform alignment in the front-back direction after performing alignment in the up-down and right-left directions.

The control unit may perform the target detecting process and the focus analyzing process while moving the optometry unit forward toward the examinee by the drive unit. Accordingly, it is possible to smoothly move the optometry unit to the focused position.

The control unit 70 may calculate the evaluation value in the entire anterior segment image or may calculate the evaluation value in an area rear the pupil. At this time, the control unit 70 may detect the pupil of the examinee's eye from the anterior segment image.

For example, when the target has been detected in the target detecting process, the control unit may continue automatic alignment. When the target has not been detected, and the examinee's eye has been detected in the image analyzing process, the control unit may stop automatic alignment after performing the automatic alignment toward the focused position on the basis of a result of the detection by the image analyzing process.

For example, when the target has been detected in the target detecting process, the control unit may execute an automatic shot after the completion of automatic alignment. When the target has not been detected, and the examinee's eye has been detected in the image analyzing process, the control unit may wait for an operation signal from an examiner without executing an automatic shot after the completion of automatic alignment based on a result of the detection by the image analyzing process.

Exemplary Embodiment

An ophthalmic apparatus according to the present disclosure will be described with reference to the drawings. Although an eye refractive power measurement apparatus will be described below as an example of the ophthalmic apparatus, the present disclosure can also be applied to other ophthalmic apparatuses such as a corneal curvature measurement apparatus, a corneal shape measurement apparatus, an eye pressure measurement apparatus, an ocular axial length measurement apparatus, a fundus camera, an optical coherence tomography (OCT), and a scanning laser ophthalmoscope (SLO).

The ophthalmic apparatus of the present exemplary embodiment, for example, examines an examinee's eye. For example, the ophthalmic apparatus of the present exemplary embodiment may examine eyes one by one or may examine both eyes at the same time (in a binocular vision). The ophthalmic apparatus mainly includes, for example, an optometry unit, a photographing unit, a drive unit, and a control unit.

<Appearance>

The appearance of the ophthalmic apparatus will be described with reference to FIG. 1. As illustrated in FIG. 1, the ophthalmic apparatus 1 of the present exemplary embodiment mainly includes an optometry unit 2, a face photographing unit 90, and a drive unit 4. The optometry unit 2 examines an examinee's eye. The optometry unit 2 may include, for example, an optical system which measures the eye refractive power, the corneal curvature, and the eye pressure of the examinee's eye. Further, the optometry unit 2 may include an optical system for photographing the anterior segment and the fundus of the examinee's eye. In the present exemplary embodiment, the optometry unit 2 which measures the refractive power will be described as an example. The face photographing unit 90, for example, photographs the face of the examinee. The face photographing unit 90, for example, photographs the face including at least one of the right and left examinee's eyes. The drive unit 4, for example, moves the optometry unit 2 and the face photographing unit 90 in the up-down, right-left, and front-back directions (the three-dimensional directions) with respect to a base 5.

Further, the ophthalmic apparatus 1 of the present exemplary embodiment may include, for example, a housing 6, a display unit 7, an operating unit 8, and a face support unit 9. For example, the housing 6 houses the optometry unit 2, the face photographing unit 90, and the drive unit 4 therein. The display unit 7, for example, displays an observation image of the examinee's eye and a measurement result. The display unit 7 may, for example, be integrated with the apparatus 1 or separated from the apparatus 1. The ophthalmic apparatus 1 may include the operating unit 8. The operating unit 8 is used in various setting operations and an operation at the time of starting a measurement of the apparatus 1. Various operation instructions by an examiner are input to the operating unit 8. For example, the operating unit 8 may be various human interfaces such as a touchscreen, a joystick, a mouse, keyboard, a trackball, and a button. The face support unit 9 may include, for example, a forehead rest 10 and a chin rest 11. The chin rest 11 may be moved in the up-down direction by driving of a chin rest driving unit 12.

<Control System>

Figure 2:
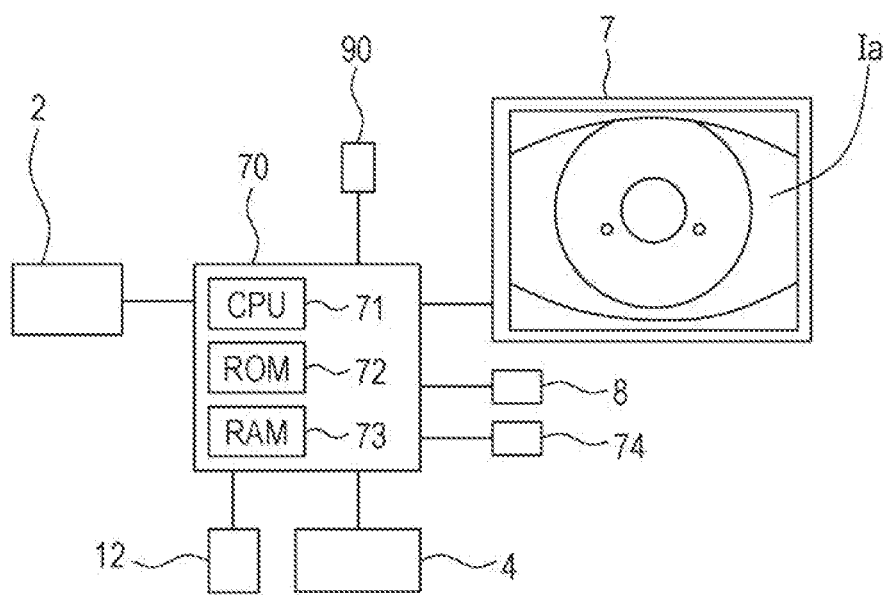
FIG. 2 is a block diagram illustrating a control system of the present exemplary embodiment.

As illustrated in FIG. 2, the apparatus 1 includes the control unit 70. The control unit 70 takes charge of various control operations of the apparatus 1. The control unit 70 includes, for example, a common central processing unit (CPU) 71, a ROM 72, and a RAM 73. For example, an ophthalmic apparatus control program for controlling the ophthalmic apparatus and an initial value are stored in the ROM 72. For example, the RAM temporarily stores various pieces of information therein. The control unit 70 is connected to the optometry unit 2, the face photographing unit 90, the drive unit 4, the display unit 7, the operating unit 8, the chin rest driving unit 12, and a storage unit (e.g., an nonvolatile memory) 74. The storage unit 74 is, for example, a non-transitory storage medium which is capable of holding stored contents even when the supply of power is cut. For example, a hard disk drive and a detachable USB flash memory can be used as the storage unit 74.

<Optometry Unit>

Figure 3:
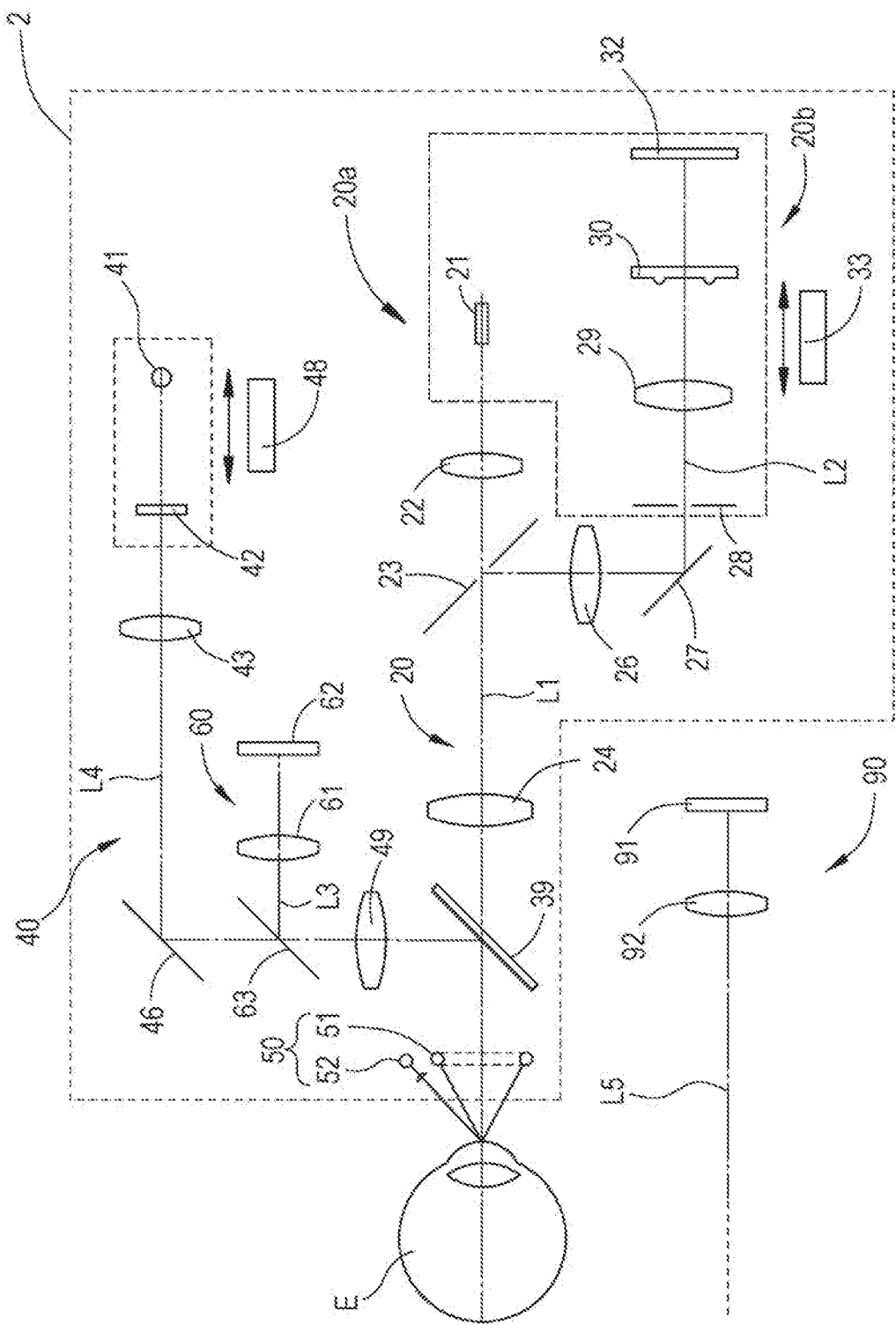
FIG. 3 is a schematic diagram illustrating an optical system of the present exemplary embodiment.

The optometry unit 2 performs a measurement, an examination, and photographing of the examinee's eye. The optometry unit 2 may include, for example, a measuring optical system which measures the refractive power of the examinee's eye. For example, as illustrated in FIG. 3, the optometry unit 2 may include a measuring optical system 20, a fixation target presenting optical system 40, a target projecting optical system 50, and an observing optical system (imaging optical system) 60.

The measuring optical system 20 may include a projecting optical system (light projecting optical system) 20a and a light receiving optical system 20b. The projecting optical system 20a projects a light flux onto the fundus Ef through the pupil of the examinee's eye. Further, the light receiving optical system 20b may capture a ring-like fundus reflected image which is mainly used in the measurement of the refractive power by extracting a reflected light flux (fundus reflected light) from the fundus Ef in a ring-like shape through a surrounding area of the pupil.

For example, the projecting optical system 20a includes a measurement light source 21, a relay lens 22, a hole mirror 23, and an objective lens 24 on an optical axis L1. The light source 21 projects a spot-like light source image onto the fundus Ef through the relay lens 22, the objective lens 24, and the pupil center part. The light source 21 is moved in the optical axis L1 direction by a moving mechanism 33. The hole mirror 23 is provided with an opening which allows the light flux from the light source 21 through the relay lens 22 to pass therethrough. The hole mirror 23 is disposed at a position optically conjugated with the pupil of the examinee's eye.

For example, the light receiving optical system 20b shares the use of the hole mirror 23 and the objective lens 24 with the projecting optical system 20a. Further, the light receiving optical system 20b includes a relay lens 26 and a total reflection mirror 27. Further, the light receiving optical system 20b includes a light receiving aperture 28, a collimator lens 29, a ring lens 30, and an imaging device 32 on an optical axis L2 in a reflection direction of the hole mirror 23. A two-dimensional photo detector such as an area CCD can be used as the imaging device 32. The light receiving aperture 28, the collimator lens 29, the ring lens 30, and the imaging device 32 are moved in the optical axis L2 direction integrally with the measurement light source 21 of the projecting optical system 20a by the moving mechanism 33. When the light source 21 is disposed at the position optically conjugated with the fundus Ef by the moving mechanism 33, the light receiving aperture 28 and the imaging device 32 are also disposed at positions optically conjugated with the fundus Ef.

The ring lens 30 is an optical device for shaping fundus reflected light guided through the objective lens 24 and the collimator lens 29 into a ring-like shape. The ring lens 30 includes a ring-like lens part and a light shielding part. Further, when the light receiving aperture 28 and the imaging device 32 are disposed at the positions optically conjugated with the fundus Ef, the ring lens 30 is disposed at a position optically conjugated with the pupil of the examinee's eye. The imaging device 32 receives ring-like fundus reflected light (hereinbelow, referred to as the ring image) through the ring lens 30. The imaging device 32 outputs image information of the received ring image to the CPU 71. As a result, the CPU 71 performs display of the ring image on the display unit 7 and calculation of the refractive power based on the ring image.

Further, as illustrated in FIG. 3, in the present exemplary embodiment, a dichroic mirror 39 is disposed between the objective lens 24 and the examinee's eye. The dichroic mirror 39 transmits light emitted from the light source 21 and fundus reflected light corresponding to the light from the light source 21. Further, the dichroic mirror 39 guides a light flux from the fixation target presenting optical system 40 (described below) to the examinee's eye. Further, the dichroic mirror 39 reflects anterior segment reflected light of light from the target projecting optical system 50 (described below) and guides the anterior reflected light to the observing optical system 60.

As illustrated in FIG. 3, the target projecting optical system 50 may be disposed in front of the examinee's eye. The target projecting optical system 50 mainly projects a target used for alignment of the optical system with respect to the examinee's eye onto the anterior segment. The target projecting optical system 50 may also be used as an anterior segment illumination which illuminates the anterior segment of an eye E.

For example, the target projecting optical system 50 may include a ring target projecting optical system 51 and a target projecting optical system 52. The ring target projecting optical system 51 projects diffusion light onto the cornea of the examinee's eye E to project a ring target (so-called Mayer ring). In the ophthalmic apparatus 1 of the present exemplary embodiment, the ring target projecting optical system 51 is also used as the anterior segment illumination which illuminates the anterior segment of the examinee's eye E. The target projecting optical system 52 projects parallel light onto the cornea of the examinee's eye to project an infinite target.

The fixation target presenting optical system 40 may be a target presenting optical system for fixing the examinee's eye. The target presenting optical system 40 includes, for example, at least a light source 41 and a fixation target 42. In FIG. 3, the light source 41, the fixation target 42, and a relay lens 43 are disposed on an optical axis L4 in a reflection direction of a reflective mirror 46. The fixation target 42 is used for being fixed by the examinee's eye in an objective refractive power measurement. The fixation target 42 is, for example, presented to the examinee's eye by illuminating the fixation target 42 by the light source 41.

The light source 41 and the fixation target 42 are integrally moved in the optical axis L4 direction by a moving mechanism 48. A presenting position (presenting distance) of the fixation target 42 may be changed by the movement of the light source 41 and the fixation target 42. Accordingly, it is possible to perform a refractive power measurement with fogging of the examinee's eye.

The anterior segment photographing optical system 60 may be provided for capturing an anterior segment image of the examinee's eye. For example, the anterior segment photographing optical system 60 includes at least an imaging lens 61 and an imaging device 62. In FIG. 3, the imaging lens 61 and the imaging device 62 are disposed on an optical axis L3 in a reflection direction of a half mirror 63. The imaging device 62 is disposed at a position optically conjugated with the anterior segment of the examinee's eye. The imaging device 62 images the anterior segment illuminated by the ring target projecting optical system 51. An output from the imaging device 62 is input to the control unit 70. As a result, an anterior segment image Ia of the examinee's eye captured by the imaging device 62 is displayed on the display unit 7 (refer to FIG. 2). Further, the imaging device 62 captures an alignment target image (in the present exemplary embodiment, the ring target and the infinite target)

which is formed on the cornea of the examinee's eye by the target projecting optical system 50. As a result, the control unit 70 can detect the alignment target image on the basis of a result of imaging by the imaging device 62. Further, the control unit 70 can determine the suitability of an alignment state on the basis of the position where the alignment target image is detected.

<Face Photographing Unit>

The face photographing unit 90 may include, for example, an optical system for photographing the face including at least one of the right and left examinee's eyes. For example, as illustrated in FIG. 3, the face photographing unit 90 of the present exemplary embodiment mainly includes, for example, an imaging device 91 and an imaging lens 92.

The face photographing unit 90 is, for example, disposed at a position where the face photographing unit 90 can photograph both examinee's eyes when the optometry unit 2 is located at an initial position. In the present exemplary embodiment, the initial position of the optometry unit 2 is set to a position displaced to the right side with respect to the examination optical axis of the optometry unit 2 so as to easily examine the right eye (refer to FIG. 4). Thus, the face photographing unit 90 is disposed at a position where the face photographing unit 90 can photographs both examinee's eyes in a state where the optometry unit 2 is located at the initial position displaced to the right side. For example, the face photographing unit 90 is disposed at a machine center M in a state where the optometry unit 2 is located at the initial position. When the initial position is set, for example, on the basis of the half of the interpupillary distance, that is, the single-eye interpupillary distance, the face photographing unit 90 may be disposed at a position displaced right or left with respect to the machine center M of the apparatus body by the single-eye interpupillary distance. The average value of the single-eye interpupillary distance is approximately 32 mm.

Further, the face photographing unit 90 may be disposed taking optical systems of various apparatuses into consideration. Optical devices such as a light source, a lens, and a photo detector may be disposed on the right and left sides of an optometry window 2*a* on the center in some apparatuses. Further, the optical devices may be disposed on the upper and lower sides of the optometry window 2*a*. Further, an air jet nozzle for eye pressure measurement may be provided. Taking the above cases into consideration, the face photographing unit 90 may be attached in an oblique direction avoiding the up-down and right-left directions of the optometry window 2*a*. In the present exemplary embodiment, the face photographing unit 90 is attached obliquely to the left of the optometry window 2*a*. In this manner, the face photographing unit 90 may be disposed taking optical systems of various apparatuses into consideration. Of course, the face photographing unit 90 may be attached in any directions around the optometry window 2*a* in some types of apparatuses.

The face photographing unit 90 of the present exemplary embodiment is moved together with the optometry unit 2 by the drive unit 4. Of course, the face photographing unit 90 may, for example, be fixed to the base 5 so as not to be moved.

Figure 5:
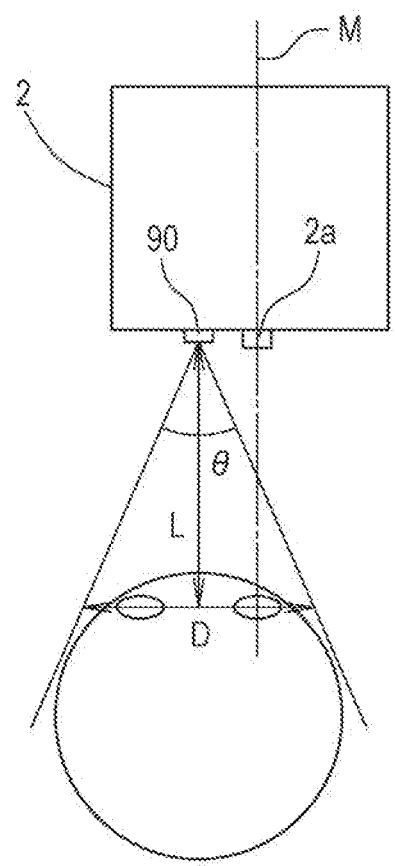
FIG. 5 is a diagram for describing a face photographing unit.

The imaging lens 92 may, for example, be a wide-angle lens. Examples of the wide-angle lens include a fisheye lens and a conical lens. The wide-angle lens enables the face photographing unit 90 to photograph the face of the examinee in a wide view angle. For example, as illustrated in FIG. 5, the following formula (1) is obtained from the relationship between a range D in which both eyes can be reliably photographed and an estimated maximum distance L from the front face of the optometry unit 2 to the examinee's eye.

[Mathematical Formula 1]

$$\theta = 2 \times \text{Tan}^{-1}\left(\frac{D/2}{L}\right) \quad (1)$$

Here, when conditions for reliably photographing both eyes when the optometry unit 2 is pulled toward the examiner as much as possible are D=100 mm and L=105 mm. θ=50.9 from formula (1). Thus, when the view angle of the face photographing unit 90 is 50° or more, it is possible to more appropriately photograph both eyes of the examinee.

<Face Illuminating Optical System>

Figure 4:
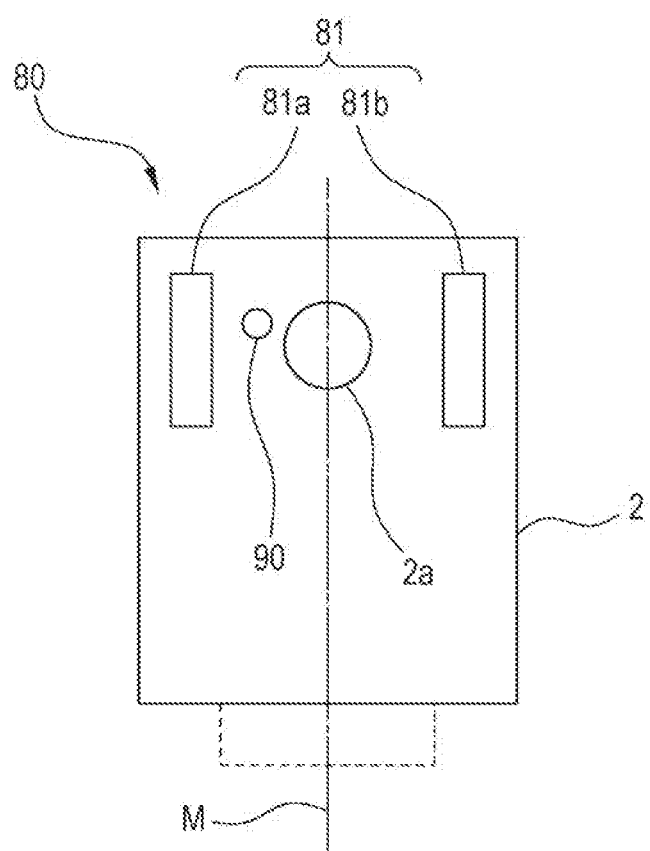
FIG. 4 is a schematic diagram illustrating an optometry unit viewed from an examinee's side.

A face illuminating optical system 80 illuminates the face of the examinee. The face illuminating optical system 80 may be provided for illuminating the face of the examinee including both eyes of the examinee. The face illuminating optical system 80 includes, for example, an illuminating light source 81. As illustrated in FIG. 4, the illuminating light source 81 includes an illuminating light source 81*a* and an illuminating light source 81*b*. The illuminating light source 81 emits infrared light. The face illuminating optical system 80 preferably illuminates the face of the examinee so that the surrounding area of the optical axis of the face photographing unit 90 is uniformly illuminated. In the present exemplary embodiment, the illuminating light sources 81 are disposed on the right and left sides of the optometry window. The illuminating light sources 81 of the face illuminating optical system 80 may be symmetrically disposed with respect to the face photographing unit 90. For example, the illuminating light sources 81 of the face illuminating optical system 80 may be symmetrically disposed right and left or symmetrically disposed up and down about the face photographing unit 90. A light source having a lower directivity than a target light source for alignment is used as the face illuminating optical system 80.

<Control Method>

Hereinbelow, a control operation of the apparatus 1 will be described. The apparatus 1, for example, fully automatically performs alignment between the optometry unit 2 and the examinee's eye for examining the examinee's eye.

Figure 6:
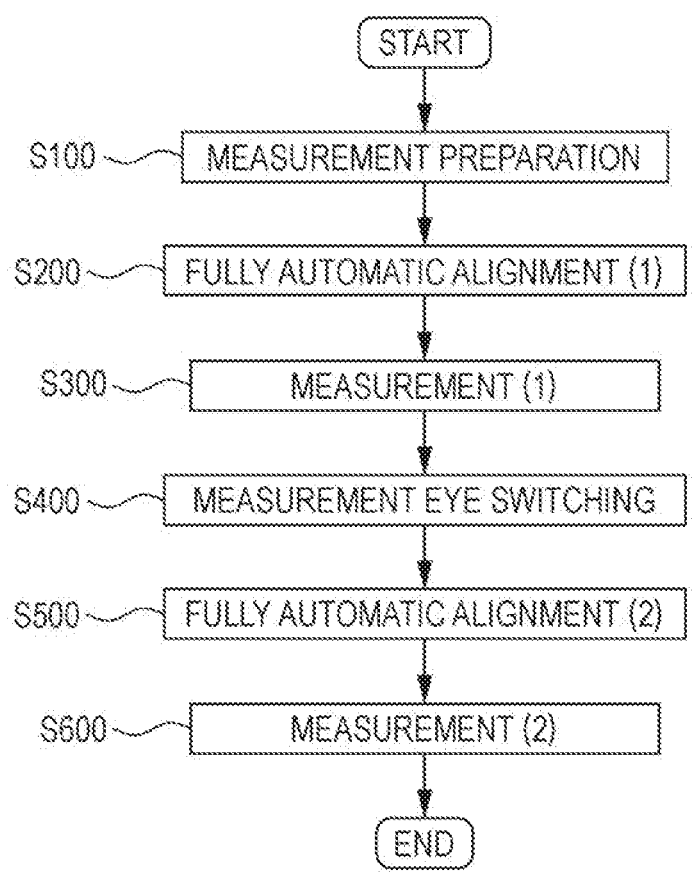
FIG. 6 is a flowchart illustrating a measurement operation of an ophthalmic apparatus.

FIG. 6 illustrates a flowchart of a fully automatic measurement. For example, the control unit 70 performs the alignment between the examinee's eye and the optometry unit 2 by performing the fully automatic alignment after performing a measurement preparation. Then, a measurement of the eye is performed, and the optometry unit 2 is moved to the other eye to perform the fully automatic alignment again. When the alignment is completed, the control unit 70 performs a measurement of the examinee's eye and finishes the process. Hereinbelow, each step will be described.

{Step S100: Measurement Preparation}

In step S100, the control unit 70 performs a measurement preparation. The details of the measurement preparation will be described below. When the measurement preparation is completed, the control unit 70 makes a shift to step S200.

{Step S200: Fully Automatic Alignment (1)}

In step S200, the control unit 70 performs fully automatic alignment with respect to one of the right and left examinee's eyes. The details of the fully automatic alignment will be described below.

{Step S300: Measurement (1)}

In step S300, the control unit 70 performs an examination of the examinee's eye. For example, the control unit 70 applies measurement light to the fundus of the examinee's eyes and measures the eye refractive power of the examinee's eye on the basis of a detection result of the measurement light reflected by the fundus.

{Step S400: Light and Left Eyes Switching}

In step S400, the control unit 70 switches the measurement target eye. For example, the control unit 70 moves the optometry unit 2 from the eye that has been examined in step S300 to the other eye.

{Step S500: Fully Automatic Alignment (2)}

In step S500, the control unit 70 performs fully automatic alignment with respect to the examinee's eye that has not yet been examined in a manner similar to step S200.

{Step S600: Measurement (2)}

In step S600, the control unit 70 performs an examination of the other examinee's eye.

<Measurement Preparation to Measurement>

Figure 7:
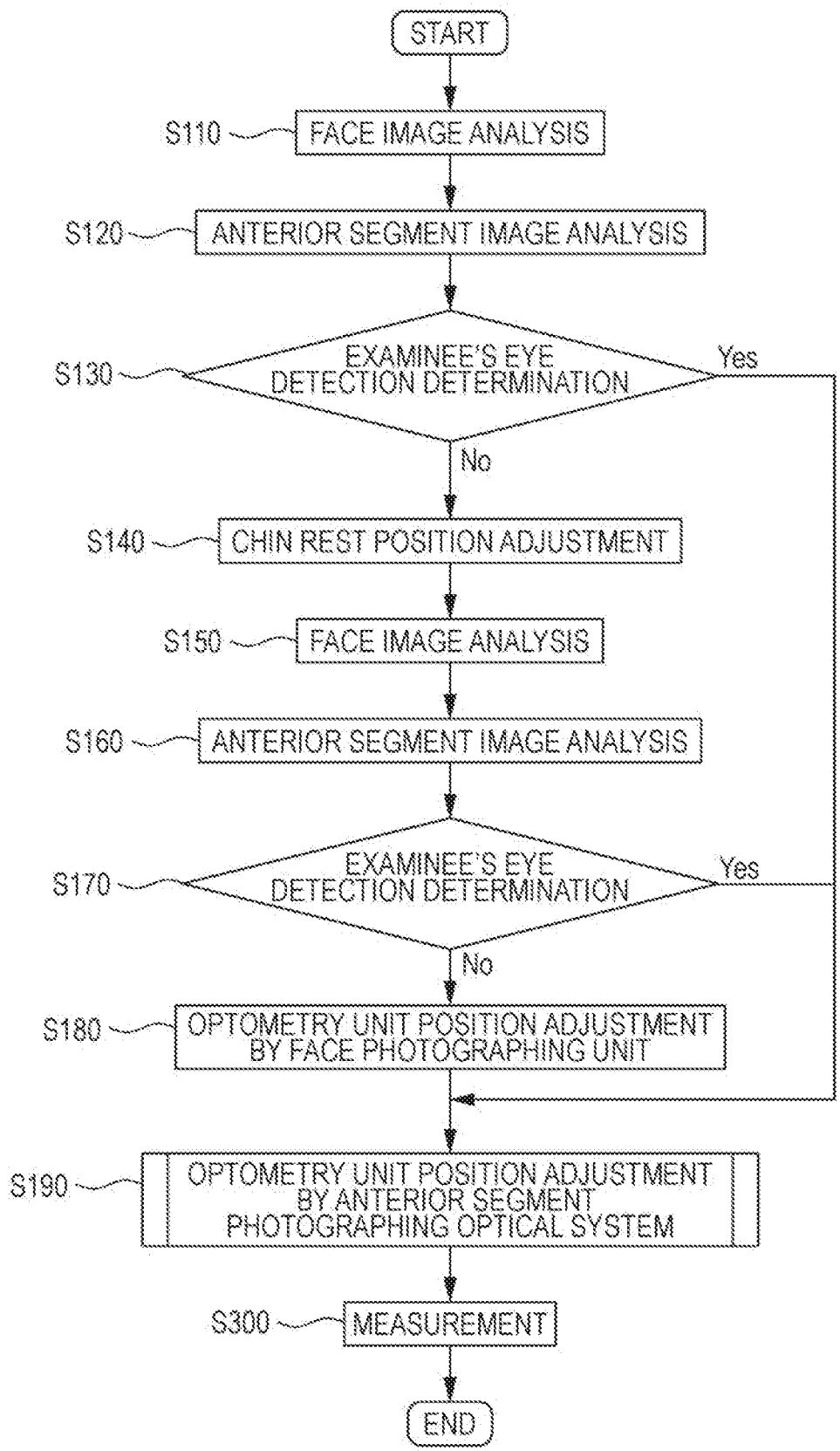
FIG. 7 is a flowchart illustrating control of a measurement preparation.

Next, control of the measurement preparation of step S100 to the measurement of step S300 will be described in more detail with reference to FIG. 7. For example, the control unit 70 detects both eyes of the examinee from a face image captured by the face photographing unit 90. Since an irradiation range of an alignment target is narrow, both eyes of the examinee cannot be illuminated. Thus, in the present exemplary embodiment, the face illuminating optical system 80 is provided. Further, after the detection of both eyes, the detection of the target or the pupil is performed. When the target or the pupil has been detected, the position of the chin rest is appropriate. Thus, the measurement preparation is finished, and a shift to a fully automatic alignment process is made. In the other cases, chin rest adjustment is performed. The chin rest adjustment may be manually performed by the examiner or automatically performed using an eye detection result previously obtained in the face photographing unit. At this time, since the pupil can be detected even when the face illumination remains on, the face illumination may remain on. Hereinbelow, each step of FIG. 7 will be described.

{Step S110: Face Image Analysis}

In step S110, the control unit 70 performs illumination of the face by the face illuminating optical system 80. For example, the control unit 70 turns on the light source 81*a* and the light source 81*b*. At this time, the control unit 70 may turn off alignment light. The control unit 70 detects at least either the right examinee's eye or the left examinee's eye on the basis of an imaging signal from the face photographing unit 90.

{Step S120: Anterior Segment Image Analysis}

In step S120, the control unit 70 performs a detection process for detecting the examinee's eye by analyzing an anterior segment image on the basis of an imaging signal from the anterior segment photographing optical system 60. For example, the control unit 70 performs a detection process for detecting the target or the pupil by analyzing the anterior segment image. At this time, the control unit 70 may turn on the alignment light and turn off the face illumination. At this time, the control unit 70 may turn on the face illumination.

{Step S130: Examinee's Eye Detection Determination}

In step S130, the control unit 70 determines whether the examinee's eyes has been detected on the basis of the imaging signal from the anterior segment photographing optical system 60 in the detection process of step S120. When the examinee's eye has been detected, the control unit 70 skips chin rest adjustment of step S140 and makes a shift to position adjustment for the optometry unit 2 by the anterior segment photographing optical system 60. When the examinee's eye has not been detected, a shift to step S140 is made.

{Step S140: Chin Rest Adjustment}

In step S140, the control unit 70, for example, adjusts the height of the chin rest by controlling the chin rest driving unit 12. The control unit 70 adjusts the height of the chin rest by controlling the chin rest driving unit 12 on the basis of an analysis result of step S110. In this case, the control unit 70 may adjust the height of the chin rest by controlling the chin rest driving unit 12 so that the examinee's eye is disposed within a movable range of the optometry unit 2. When the chin rest adjustment is not necessary, a shift to step S180 may be made.

According to the above flow, at least the chin rest adjustment can be skipped when the adjustment of the height of the chin rest does not necessarily have to be performed, by performing the eye detection based on the imaging signal from the anterior segment photographing optical system 60 in the chin rest adjustment based on the imaging signal from the face photographing unit 90. Thus, the alignment with respect to the examinee's eye can be smoothly performed.

{Step S150: Second Face Image Analysis}

When the adjustment of the height of the chin rest is completed, the control unit 70 detects at least either the right examinee's eye or the left examinee's eye on the basis of the imaging signal from the face photographing unit 90 in step S150.

{Step S160: Second Anterior Segment Image Analysis}

In step S160, the control unit 70 performs a detection process for detecting the examinee's eye by analyzing the anterior segment image on the basis of the imaging signal from the anterior segment photographing optical system 60. At this time, the control unit 70 may turn on the alignment light and turn off the face illumination. At this time, the control unit 70 may turn on the face illumination.

{Step S170: Second Examinee's Eye Detection Determination}

In step S170, the control unit 70 determines whether the examinee's eye has been detected in the detection process of step S160. When the examinee's eye has been detected, the control unit 70 skips position adjustment for the optometry unit 2 by the face photographing unit 90 and makes a shift to position adjustment for the optometry unit 2 by the anterior segment photographing optical system 60. When the examinee's eyes has not been detected, a shift to step S180 is made.

{Step S180: Position Adjustment by Face Photographing Unit}

In step S180, the control unit 70, for example, adjusts the position of the optometry unit 2 by controlling the drive unit 4 on the basis of an imaging signal from the face photographing unit 90. The control unit 70 detects the position of the examinee's eye on the basis of the imaging signal from the face photographing unit 90. The control unit 70 adjusts the position of the optometry unit 2 by controlling the drive unit 4 on the basis of the position detection result. In this case, the control unit 70 may adjust the position of the optometry unit 2 by controlling the drive unit 4 so that the examinee's eye is disposed within a photographable range by the anterior segment photographing optical system 60.

{Step S190: Position Adjustment by Anterior Segment Photographing Optical System 60}

In step S190, the control unit 70 adjusts the position of the optometry unit 2 by controlling the drive unit 4 on the basis of an imaging signal from the anterior segment photographing optical system 60. The control unit 70 detects the position of the examinee's eye on the basis of the imaging signal from the anterior segment photographing optical system 60. The control unit 70 adjusts the position of the optometry unit 2 by controlling the drive unit 4 on the basis of the position detection result. In this case, the control unit 70 may adjust the position of the optometry unit 2 by controlling the drive unit 4 so that the examinee's eye is disposed within an alignment allowable range.

According to the above flow, the control of movement of the optometry unit 2 by the face photographing unit 90 can be skipped when the movement of the optometry unit 2 by the face photographing unit 90 does not necessarily have to be performed by performing the eye detection based on the imaging signal from the anterior segment photographing optical system 60 in the optometry unit position adjustment based on the imaging signal from the face photographing unit 90. Thus, the alignment with respect to the examinee's eye can be smoothly performed.

<Parallel Processing of Target Detection and Examinee's Eye Detection Different from Target Detection>

Figure 8:
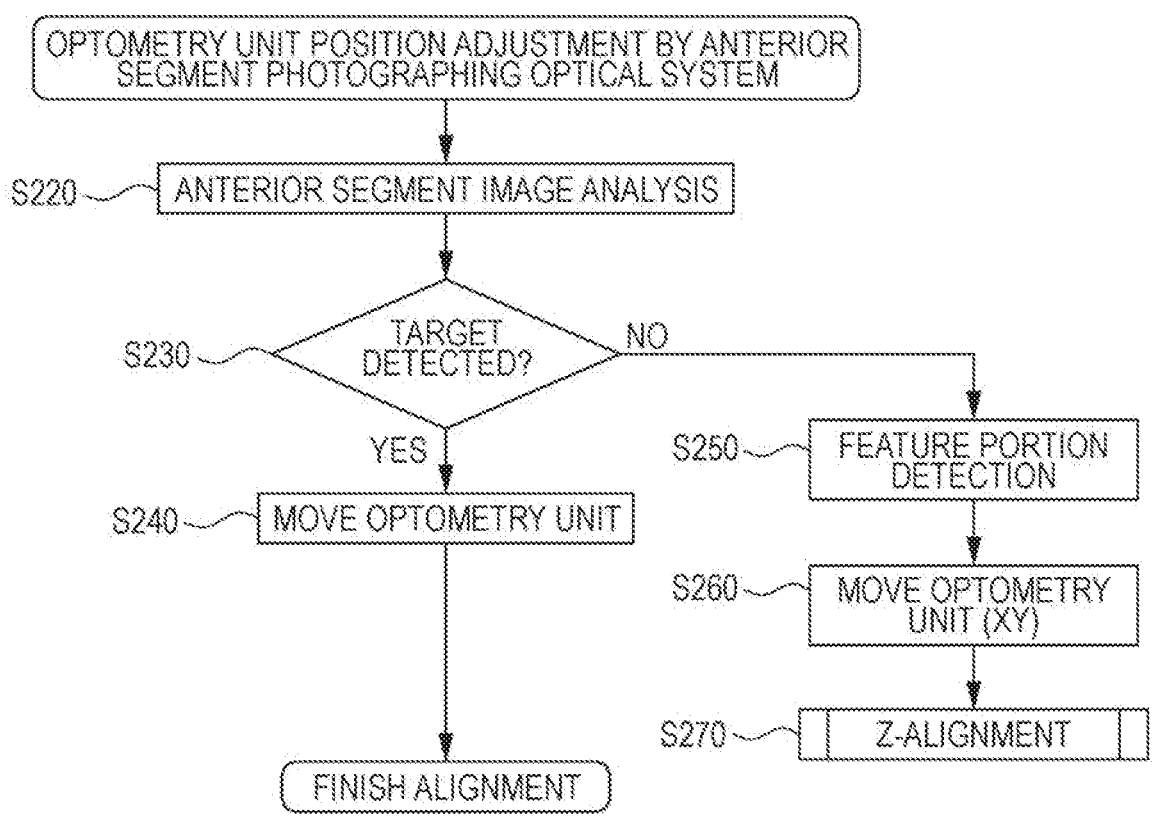
FIG. 8 is a flowchart illustrating control of fully automatic alignment.

Next, an example of the control in step S190 will be described with reference to FIG. 8. In step S190, the control unit 70 may perform target detection in the anterior segment image in parallel with examinee's eye detection different from the target detection on the basis of the imaging signal from the anterior segment photographing optical system 60. In the following description, the case where the examinee's eye is detected by detecting a feature portion of the examinee's eye will be described as an example of the examinee's eye detection different from the target detection.

In this case, when the target has been detected, the control unit 70 moves the optometry unit 2 relative to the examinee's eye by controlling the drive unit 4 on the basis of the detected target. When the target has been not detected, and the feature portion of the examinee's eye has been detected, the control unit 70 performs XY-alignment by controlling the drive unit 4 on the basis of a result of the detection of the feature portion and performs Z-alignment (described below).

The control unit 70 may turn off the face illumination after the completion of the XY-alignment using the feature portion. This is because the face illuminating light appears as a raster, which may become an impediment to the target detection. Of course, the present exemplary embodiment is not limited thereto, and the face illumination may be turned off at the point when a change to the optometry unit movement using the anterior segment photographing optical system 60 is made. Further, the control unit 70 may turn off the face illumination and perform severe alignment between the examinee's eye and the optometry unit 2 when a deviation in the alignment between the examinee's eye and the optometry unit 2 reaches the predetermined alignment range after the execution of automatic alignment using the target. Hereinbelow, each step of FIG. 8 will be described.

{Step S220: Anterior Segment Image Analysis}

In step S220, the control unit 70, for example, performs a detection process for detecting at least either the feature portion of the examinee's eye or the target from an anterior segment image captured by the anterior segment photographing optical system 60.

{Step S230: Target Detection Determination}

In step S230, the control unit 70, for example, determines whether the target has been detected in the detection process of step S220. The control unit 70 makes a shift to step S240 when the target has been detected and makes a shift to a process of step S250 when the target has not been detected.

{Step S240: Alignment}

In step S240, the control unit 70, for example, moves the optometry unit 2 by controlling driving of the drive unit 4 on the basis of positional information of the target detected in the anterior segment image analysis of step S220. The control unit 70 finishes the fully automatic alignment after moving the optometry unit 2.

{Step S250: Feature Portion Detection}

In step S250, the control unit 70, for example, detects the feature portion from the anterior segment image. The control unit 70 may make a return to step S180 or perform error handling when the feature portion has not been detected.

{Step S260: Pupil Alignment (XY)}

In step S260, the control unit 70, for example, moves the optometry unit 2 by controlling driving of the drive unit 4 on the basis of positional information of the feature portion detected in step S220. For example, the control unit 70 moves the optometry unit 2 so that reference coordinates (e.g., pupil center coordinates) of the feature portion detected by the anterior segment image analysis of step S220 are located at an aimed position on the image.

{Step S270: Z-Alignment}

In step S270, the control unit 70, for example, performs alignment in the Z direction. The details of the Z-alignment will be described below.

As described above, the alignment between the optometry unit 2 and the examinee's eye can be reliably performed by performing the alignment by the examinee's eye detection whose detectable range is wider than the target detection in parallel with the alignment by the target detection.

There has been described that the target detection and the detection of the feature portion of the examinee's eye different from the target detection are performed at the same time. However, a deviation in timing with which a displacement of an observation point caused by rough alignment movement is negligible is allowed. For example, the target detection and the feature portion detection may be alternately performed for each frame. In such a case, setting of the camera and preprocessing on an image may be changed between the target detection and the feature portion detection. For example, during the feature portion detection, a gamma correction may be performed in order to enhance the contrast between a predetermined feature portion and the other portion.

In a manner similar to the above method, the control unit 70 may perform the target detection in the face image in parallel with the examinee's eye detection different from the target detection on the basis of the imaging signal from the face photographing unit 90. In this case, at least either parallel detection based on the imaging signal from the face photographing unit 90 or parallel detection based on the imaging signal from the anterior segment photographing optical system 60 may be performed.

Figure 9:
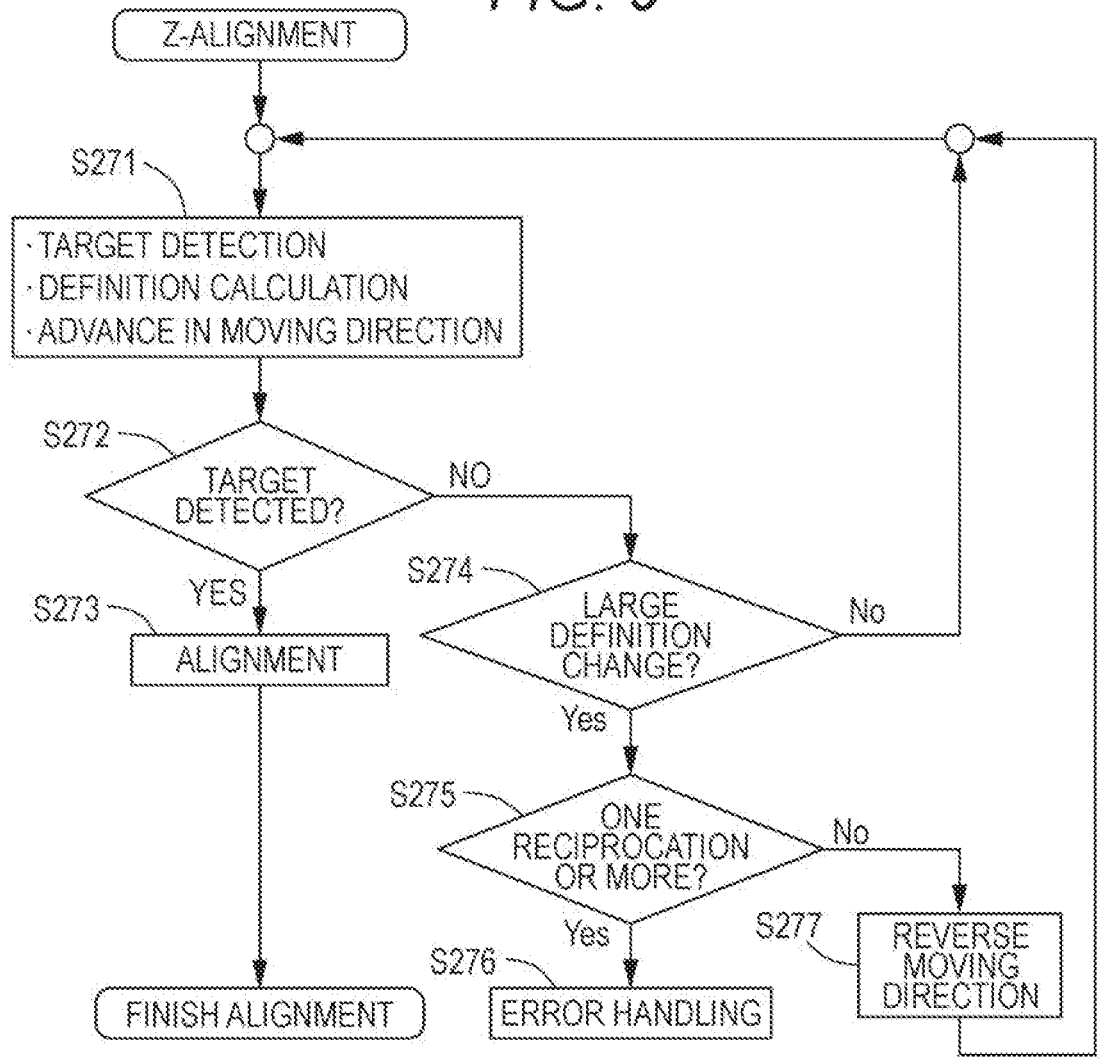
FIG. 9 is a flowchart illustrating control of Z-alignment.

Next, the Z-alignment of step S270 will be described. In the present exemplary embodiment, the control unit 70 advances the optometry unit 2 in the Z direction while performing target detection and performs alignment when the target is detected. Further, the control unit 70, for example, calculates the sharpness of the anterior segment image in parallel with the target detection in order to efficiently make a search for the position where the target can be detected. Hereinbelow, each step of FIG. 9 will be described.

{Step S271: Target, Definition Calculation, Advance in Moving Direction}

In step S271, the control unit 70, for example, moves the optometry unit 2 in the Z direction by controlling driving of the drive unit 4. At the beginning, the control unit 70 moves the optometry unit 2 forward in a direction approaching the examinee's eye. The control unit 70 performs the target detection and the definition calculation while moving the optometry unit 2 forward. The definition of the image is high at a position in focus and, on the other hand, low at an out-of-focus position. For example, the control unit 70 determines whether the optometry unit 2 has moved closer to the focused position or moved away from the focused position as a result of the movement on the basis of the change amount in the definition before and after the movement in the Z direction. The change amount in the definition cannot be known before the movement in the Z direction. Thus, the change amount cannot be used in the determination of the moving direction at a start position. Thus, the start position may be set to a front focus position (the position before the focused position) so that the optometry unit 2 can move in an appropriate direction even when the target cannot be detected at the start position.

The target detection and the sharpness calculation may be simultaneously performed. Alternatively, the target detection and the sharpness calculation may be performed at different timings when a displacement of the observation point caused by the movement of the optometry unit 2 in the focus direction is negligible. For example, the control unit 70 may alternately perform the target detection and the sharpness calculation for each frame.

{Step S272: Target Detection Determination}

In step S272, the control unit 70 determines whether the target for alignment has been detected by the anterior segment image analysis in the middle of moving the optometry unit 2 forward. The control unit 70 makes a shift to step S273 when the target has been detected and makes as shift to step S274 when the target has not been detected.

{Step S273: Alignment}

In step S273, the control unit 70 performs alignment on the basis of positional information of the target calculated in step S271 and finishes the alignment.

{Step S274: Definition Change Amount Determination}

In step S274, the control unit 70 determines whether the definition change amount calculated in step S271 is large. For example, when the optometry unit 2 has passed the focused position with the target remaining undetected, the definition is largely reduced. The control unit 70 makes a shift to step S275 when the definition change amount is large and makes a return to step S271 when the definition change amount is small.

{Step S275: Reciprocation Determination}

In step S275, the control unit 70, for example, determines whether the number of reciprocations, which is the number of repetitions of forward and backward movements, is one or more. The control unit 70 makes a shift to step S276 when the number of reciprocations is one or more and makes a shift to step S277 when the number of reciprocations is less than one.

{Step S276: Error Handling}

In step S276, the control unit 70 determines an alignment error and performs error handling. For example, the control unit 70 may perform a movement to a focus position where the sharpness becomes maximum between the front focus and a rear focus (the rear position relative to the focused position) and notify the examiner or the examinee that the alignment has been failed by a display or a voice reproduction. Further, in this case, the control unit 70 may switch the alignment mode from the fully automatic mode to a manual mode.

Further, the control unit 70 may perform a measurement at the focus position where the sharpness becomes maximum instead of the error handling. In this case, the fact that the measurement position is not the position of the target alignment may be displayed together with a measurement result.

{Step S277: Moving Direction Reversal}

In step S277, the control unit 70, for example, reverses the moving direction of the optometry unit 2. For example, the control unit 70 reverses the moving direction when the sharpness is largely reduced. This process enables a prompt return even when the optometry unit 2 has passed the appropriate position. The control unit 70 makes a return to step S271 after reversing the moving direction.

As described above, the optometry unit 2 can be smoothly moved to the position where the target alignment can be performed by performing the target detection process in parallel with the sharpness calculation process from the anterior segment image. Even for a sick eye in which the alignment using the target is difficult, it is possible to move optometry unit 2 close to the alignment position as described in the present exemplary embodiment.

Further, the method using the sharpness of the anterior segment image does not depend on the shape of the alignment target. Thus, the method using the definition of the anterior segment image can be used in various apparatuses that perform alignment by the anterior segment image analysis. Further, this can also be used in an ophthalmic apparatus that starts alignment on the basis of an initial point (e.g., the pupil position) which is manually given.

<Sharpness Calculation>

An example of the calculation of the sharpness will be described. In the present exemplary embodiment, an edge intensity is calculated as the sharpness. For example, the control unit 70 calculates the edge intensity by convoluting (processing from up and down and right and left) a Sobel filter (a one-dimensional filter for outline detection) into the anterior segment image. The edge intensity is a change state of the brightness at some point, and a value of the edge intensity becomes larger as the outline is clearer. For example, the control unit 70 determines an integral value of the edge intensity in the entire image (a total value of the edge intensity in the entire image) as a focus evaluation value. When Gx (x, y) denotes a luminance gradient in the x direction of coordinates (x, y) obtained by the convolution of the Sobel filter, and Gy (x, y) denotes a luminance gradient in the y direction, a luminance gradient intensity G (x, y) is given by the following formula (2).

[Mathematical Formula 2]

$$G(x,y) = \sqrt{(G_x(x,y))^2 + (G_y(x,y))^2} \quad (2)$$

A focus evaluation value F is given by the following formula (3) from the integral value of G (x, y).

[Mathematical Formula 3]

$$F = \sum_{i=0}^{i=W} \sum_{j=0}^{j=H} G(i, j) \quad (3)$$

Here, W denotes the width (pixel) of the image, and H denotes the height (pixel) of the image. Although the Sobel filter is used in this example, another filter such as a Prewitt filter may be used. Further, although the integral value of the edge intensity in the entire image is used, an area is not limited thereto. For example, the area may be only an area near the center of the image. Further, the contrast of the image may be used instead of the edge intensity.

Figure 10:
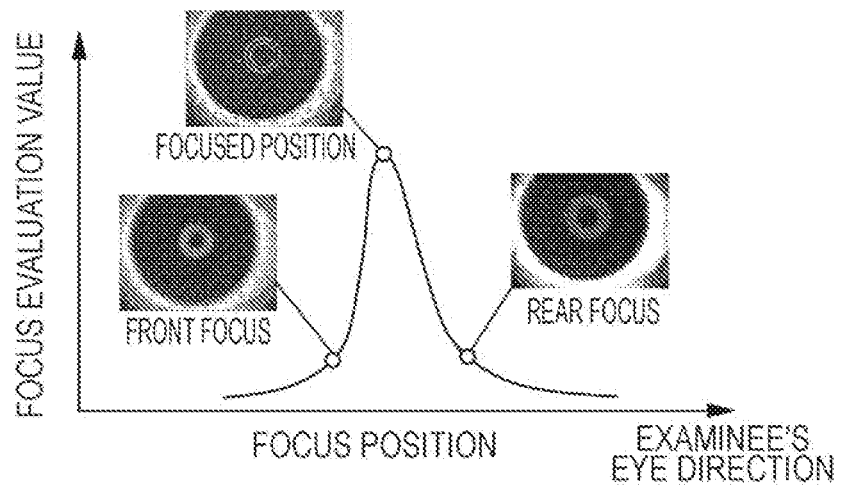
FIG. 10 is a diagram illustrating the relationship between a focus position and a focus evaluation value.

Next, an example of the sharpness change amount determination will be described. In the exemplary embodiment, the control unit 70 obtains the change amount in the sharpness between a Z-position where the sharpness becomes maximum and a position after the movement in the Z direction in the detection. FIG. 10 is a graph illustrating the relationship between the focus position and the focus evaluation value. As illustrated in FIG. 10, the focus evaluation value has a peak (maximum value) at the focused position and has low values at the front focus and the rear focus.

Here, F (Z) denotes the focus evaluation value at the focus position Z. For example, the control unit 70 determines that the change amount in the sharpness is large when the condition of the following formula (4) is satisfied.

[Mathematical Formula 4]

$$F(Z) < \alpha F(Z_{max}) \quad (4)$$

Note that $\alpha$ is a constant. Further, $\alpha$ may be an empirically obtained value. In the present exemplary embodiment, $\alpha$ is 2/3. Further, Zmax is, for example, a Z-position where the sharpness becomes maximum in the detection. When there is a sufficient difference between the sharpness at the position Z and the maximum value, the condition of formula (4) is satisfied. On the other hand, only an out-of-focus position is observed or only a position near the focused position can be observed, the condition of formula (4) is not satisfied. When the control unit 70 determines that the condition of formula (4) is satisfied, the control unit 70 determines that the change amount in the sharpness is large, and the position has moved away from the focused position.

Examples of the method for detecting the examinee's eye from the image include various image processing methods such as pupil detection by infrared photographing and edge detection in a luminance value. For example, when the face of the examinee is photographed with infrared light, the skin appears white, and the pupil appears black. Thus, the control unit 70 may detect a black round part (part having a low luminance) as the pupil from an infrared image obtained by the infrared photographing. The control unit 70 detects the examinee's eye from the face image If and acquires two-dimensional positional information of the examinee's eye by using the method as described above.

Although, in the present exemplary embodiment, final alignment is performed by detecting the alignment target in the anterior segment image Ia captured by the anterior segment photographing optical system 60, the final alignment is not limited thereto. For example, the control unit 70 may perform the final alignment using the pupil position, the contrast, or the edge of the anterior segment image Ia.

The face photographing unit 90 may be disposed at the same height as the height of the optical axis of the optometry unit 2. For example, the height of the optical axis of the face photographing unit 90 may be equal to the height of the optical axis of the optometry unit 2. Accordingly, for example, the face photographing unit 90 can also align the height of the optometry unit 2 with the examinee's eye by aligning the height of the face photographing unit 90 with the examinee's eye.

As a simplest method, the control unit 70 may set the depth position of the optometry unit 2 at the position farthest from the examinee and then slowly advance the optometry unit 2 toward the examiner until the target can be detected.

LIST OF REFERENCE NUMERALS

1 ophthalmic apparatus
2 optometry unit
4 drive unit
5 base
6 housing
70 control unit
71 CPU
72 ROM
73 RAM
80 face illuminating optical system
90 face photographing unit

What is claimed is:

1. An ophthalmic apparatus that examines an examinee's eye, the ophthalmic apparatus comprising:
    an optometry unit that examines an examinee's eye;
    drive means that adjusts a relative position between the optometry unit and an examinee's eye;
    an illuminating optical system including a first illuminating optical system for illuminating an anterior segment of an examinee's eye and a second illuminating optical system for illuminating a wider range than the first illuminating optical system;
    an imaging optical system including a first imaging optical system for imaging an anterior segment of an examinee's eye and a second imaging optical system for imaging a wider range than the first imaging optical system; and
    a processor that controls an illuminating state with respect to an anterior segment between anterior segment illumination by the first illuminating optical system and wide range illumination by the second illuminating optical system, wherein
    the processor switches the imaging optical system in alignment of the optometry unit between the first imaging optical system and the second imaging optical system,
    the processor restricts illumination by the second illuminating optical system in the alignment of the optometry unit using the first imaging optical system, and
    when the processor switches the imaging optical system used in the alignment of the optometry unit between the first imaging optical system and the second imaging optical system, the processor performs switching between the anterior segment illumination by the first illuminating optical system and the wide range illumination by the second illuminating optical system.

2. The ophthalmic apparatus according to claim 1, wherein
    the second illuminating optical system is disposed at a different position with respect to at least a part of the first illuminating optical system.

3. The ophthalmic apparatus according to claim 1, wherein
    the illuminating state with respect to the examinee is controlled on the basis of an imaging signal from the imaging optical system.

4. The ophthalmic apparatus according to claim 1, wherein
    the processor restricts illumination by the first illuminating optical system in the alignment of the optometry unit using the second imaging optical system.

5. The ophthalmic apparatus according to claim 1, wherein
the processor controls the drive unit on the basis of imaging signals from the first imaging optical system and the second imaging optical system.

6. An ophthalmic apparatus that examines an examinee's eye, the ophthalmic apparatus comprising:
an optometry unit that examines an examinee's eye;
drive means that adjusts a relative position between the optometry unit and an examinee's eye;
an illuminating optical system including a first illuminating optical system for illuminating an anterior segment of an examinee's eye and a second illuminating optical system for illuminating a wider range than the first illuminating optical system;
an imaging optical system including a first imaging optical system for imaging an anterior segment of an examinee's eye and a second imaging optical system for imaging a wider range than the first imaging optical system; and
a processor that switches the imaging optical system in alignment of the optometry unit between the first imaging optical system and the second imaging optical system, wherein
the second illuminating optical system is disposed at a different position with respect to at least a part of the first illuminating optical system,
the processor restricts illumination by the second illuminating optical system in the alignment of the optometry unit using the first imaging optical system, and
when the processor switches the imaging optical system used in the alignment of the optometry unit between the first imaging optical system and the second imaging optical system, the processor performs switching between anterior segment illumination by the first illuminating optical system and wide range illumination by the second illuminating optical system.

7. The ophthalmic apparatus according to claim 1, wherein the second illuminating optical system is a face illuminating optical system, and an illumination range of the second illuminating optical system is an illumination range capable of illuminating a face of an examinee including at least both eyes.

8. The ophthalmic apparatus according to claim 1, wherein the second imaging optical system is a face imaging optical system for imaging a face of an examinee including at least both eyes.

* * * * *